United States Patent [19]
Peck et al.

[11] Patent Number: 5,107,713
[45] Date of Patent: Apr. 28, 1992

[54] AIR SAMPLING PUMP

[75] Inventors: Richard W. Peck; Timothy L. Nash, both of Lynchburg, Va.; Albert P. Buck, Orlando; Roger H. Motten, Deltona, both of Fla.

[73] Assignee: A.P. Buck, Inc., Orlando, Fla.

[21] Appl. No.: 495,273

[22] Filed: Mar. 16, 1990

[51] Int. Cl.⁵ .............................................. G01N 1/24
[52] U.S. Cl. ............................ 73/863.02; 73/864.34; 364/496
[58] Field of Search ........... 73/863.02, 863.03, 864.34, 73/864.35; 364/496

[56] References Cited

U.S. PATENT DOCUMENTS

| | | | |
|---|---|---|---|
| 4,123,932 | 11/1978 | Baker et al. | 73/28.01 |
| 4,241,299 | 12/1980 | Bertone | 318/474 |
| 4,269,059 | 5/1981 | Baker | 73/28.01 X |
| 4,389,903 | 6/1983 | Bertone et al. | 73/863.03 |
| 4,432,248 | 2/1984 | Lalin | 73/863.03 |
| 4,527,953 | 7/1985 | Baker et al. | 417/38 |
| 4,586,367 | 5/1986 | Lewis | 73/23.33 |
| 4,860,590 | 8/1989 | Buck | 73/861.05 |
| 4,893,515 | 1/1990 | Uchida | 73/864.34 |

Primary Examiner—Tom Noland
Attorney, Agent, or Firm—James H. Beusse

[57] ABSTRACT

A microprocessor controlled air sampling pump utilizes a PWM controlled DC electric motor for regulating air flow generated by a diaphragm-type air pump. The control system regulates air flow as a function of RPM of the motor by establishing a table of values which relate motor RPM to air flow rates. The control system maintains RPM at the desired value but includes a control loop which senses deviations in RPM and adjusts the PWM signals to the motor to regulate RPM. The system also senses large changes in RPM and treats such changes as blockages in the air sampling pump lines which prevent accurate environmental sampling. This system enters a cycling mode which turns the pump motor off for different time intervals until the detected blockage has been removed or until a predetermined time has expired. This procedure minimizes battery drain in the event of blockage of the air sampling pump lines. It also provides a method of accurately monitoring pump run time since it shuts off the pump during times in which the air flow is blocked.

5 Claims, 5 Drawing Sheets

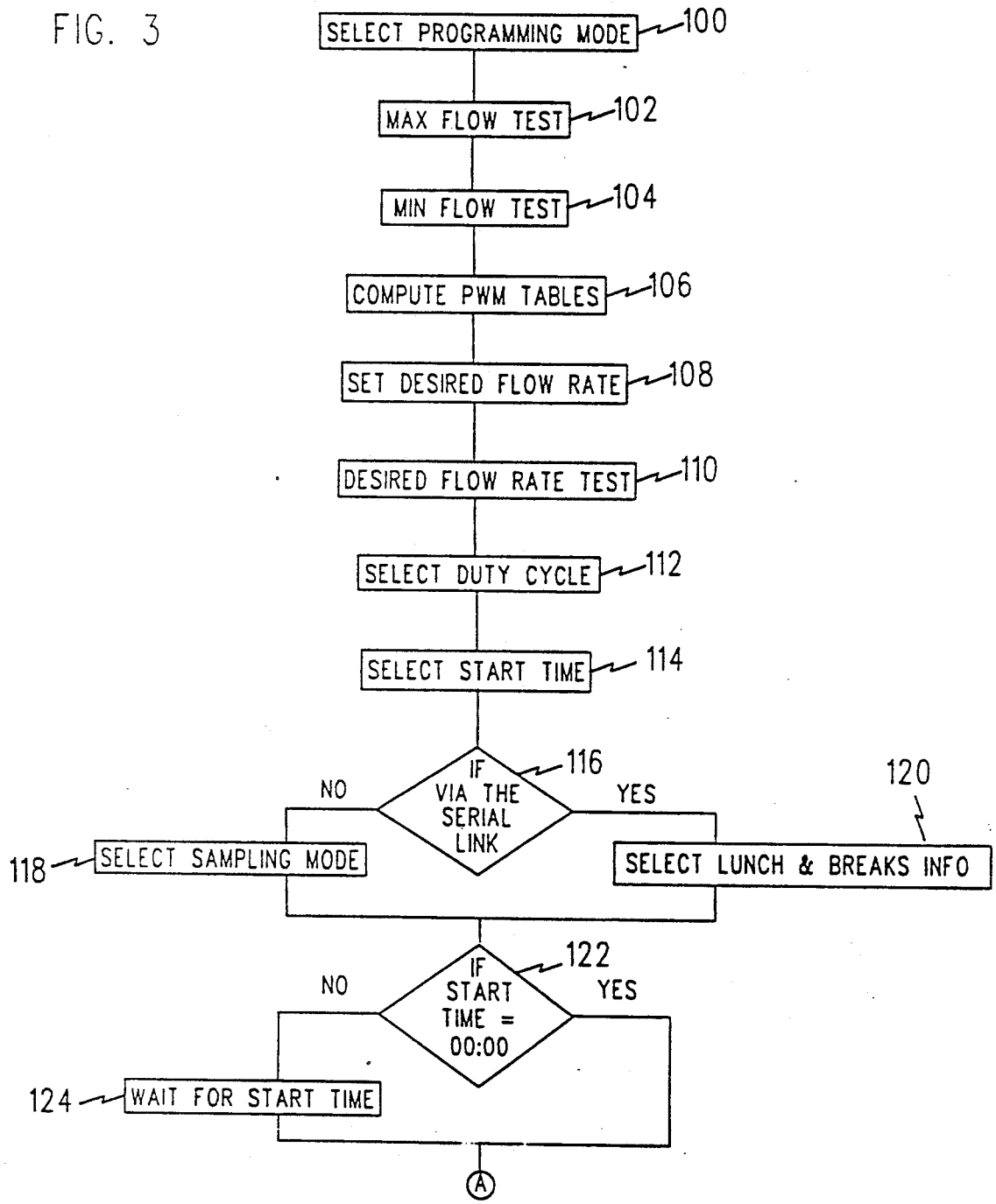

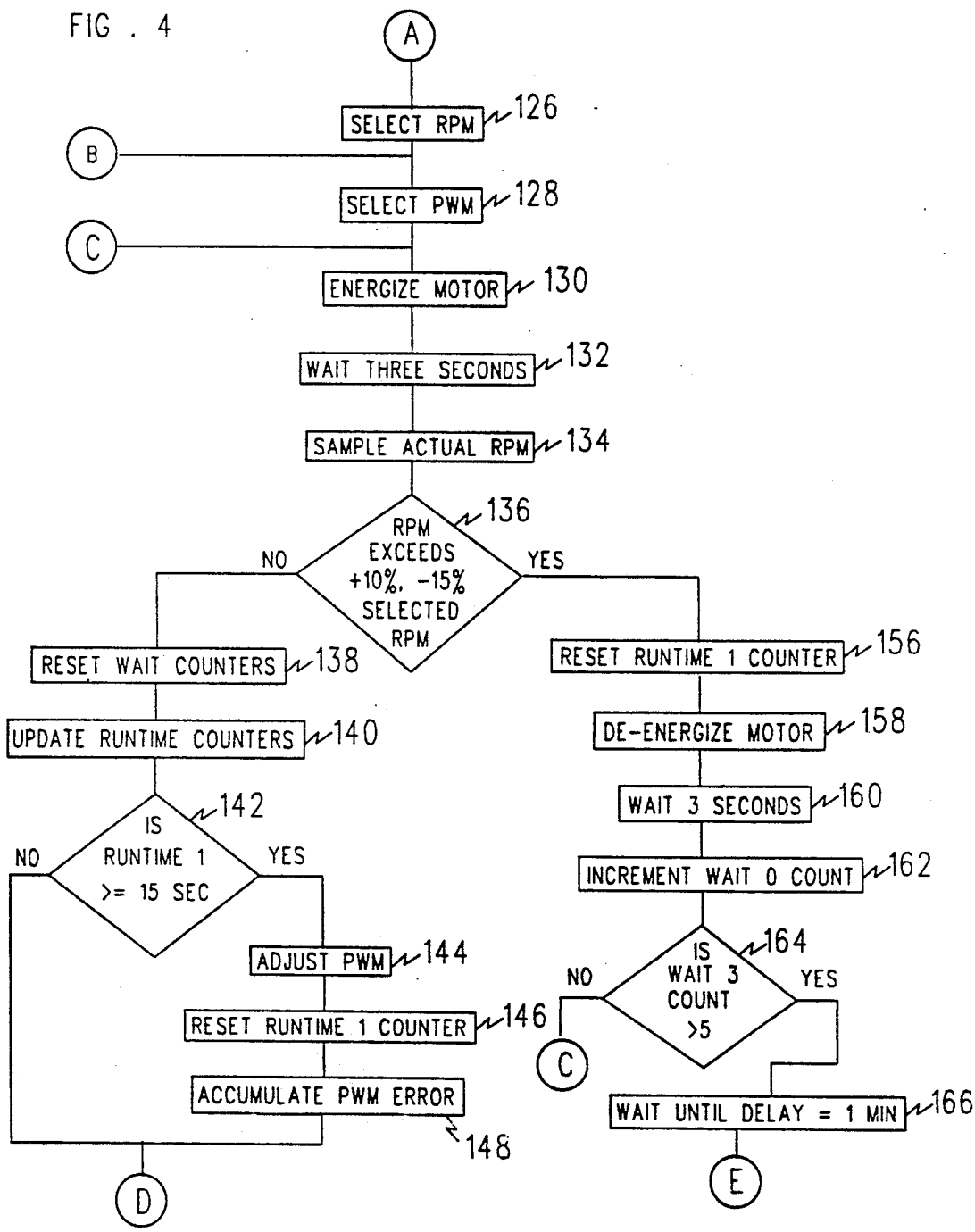

AIR SAMPLING PUMP

BACKGROUND OF THE INVENTION

This invention relates to battery powered gas sampling pump devices small enough to collect environmental air samples on individual workers.

Traditional personal air sampling techniques utilize air flow rates of about 2,000 cc/minute. However, flows may be necessary as low as 5 cc/minute and for sample bag filling, may go up to 4,000 cc/minute. It is therefore desirable to provide variable flow rates from 5 cc/minute to 4,000 cc/minute with a controlled flow system. It is also desirable to provide for accurate volume samples of 3% or lower by controlling the pump flow. It is further desirable to have a self-calibrating flow system incorporated in the pump system which can compare pump flow rate against a primary flow calibrator such as that shown in U.S. Pat. No. 4,860,590.

It is also desirable to accurately monitor pump run time. It is believed that the ability to time air flow blockage or sudden removal of an air filter has not heretofore been available so as to provide accurate run time data. In addition, it is desirable to provide a system which maintains all air sampling information in the event of a battery failure.

SUMMARY OF THE INVENTION

It is an object of the present invention to provide an air sampling pump system which provides the above and other desirable features.

It is another object to provide an air flow sampling system which avoids the use of pressure switches, orifices, or elaborate pressure regulated flow control systems.

It is still another object to provide an air flow sampling system which accurately measures air flow and pump run time using only pump motor speed and an initial measured flow rate.

The air sampling pump, in a preferred embodiment, utilizes a 16-bit embedded controller microprocessor for a compact design with a small power supply for ease of the individual to wear. The pump measures 4"×5⅜"×2⅛" and, with battery pack, weighs about twenty-three ounces. This type of CPU use allows control of various analog signals including an opto-electronic RPM sensor, ambient air temperature, battery reference voltage, low flow bypass switch, and serial communication. A lithium long life battery serves as a backup for memory data storage. Timing is accurately driven by pulse width modulation (PWM), an internal feature of the CPU.

In accordance with this invention, the pump controls loading and flow regulation by use of an opto-electronic revolution per minute (RPM) counter and PWM for measured flow rates. Gases drawn into the pump are filtered by an integral built-in 50 micron pore size filter, a part of a damping chamber. The damping chamber serves to remove pulsing from the single diaphragm pump. A bypass valve is an integral part of the pump body and is turned about 30 degrees to function. In bypass mode, a switch alerts the CPU to low flow status. The bypass valve recirculates a large portion of the inlet air and allows flow to be reduced to accommodate very low flows. Flow is adjusted by a remote needle valve at the input filter. The bypass valve prevents overloading of the pump on low flow sampling.

In a preferred form, the system comprises an air sampling pump having a central processing unit (CPU) for developing pulse width modulation (PWM) control signals for application to a PWM motor driver which is connected to a DC electric motor. The motor is coupled in driving relationship to a diaphragm-type air pump and a revolution per minute (RPM) counter is coupled to the motor for providing RPM signals representative of air flow. The CPU includes memory operatively associated with it for storing data indicative of relationships between RPM, PWM, and air flow. The CPU is responsive to a commanded air flow signal for generating a corresponding PWM signal for energizing the motor at a preselected RPM. In a preferred form, the pump is first energized at a preselected PWM value and the pump flow rate and RPM's corresponding to the PWM value are recorded. The pump is then energized at another preselected PWM value and the pump flow rate and RPM corresponding to that value are also recorded. These two values enable development of a characteristic curve for the pump filter combination. The CPU creates tables of PWM values relating RPM and flow rate to PWM values for a range of values including the first and another PWM value. A desired flow rate is then set in the CPU using keyboard entry so that the CPU generates a first PWM signal to energize the pump at an RPM corresponding to the desired flow rate. The RPM of the pump is monitored and the PWM value is periodically adjusted to maintain the RPM at the selected value. If the actual difference between the actual RPM and the selected RPM exceeds a preselected value, the table of values relating RPM to PWM may be adjusted to compensate the RPM values proportionately to the actual difference. This process accounts for gradual clogging of the air inlet filter as samples are collected. In another form, the system detects any abrupt changes in the actual RPM and de-energizes the pump motor for preselected time intervals. This portion of the method accommodates kinking of the air hose leading to the air inlet and minimizes battery drain by turning off the pump if the air hose becomes kinked. The method includes cycling the pump at short on and off intervals for a preselected number of times, thereafter cycling it for longer off periods for another preselected number of intervals, and finally cycling for even longer time intervals before finally indicating an abort and shutting down the system. The method includes recording of the time that the pump actually ran.

BRIEF DESCRIPTION OF THE DRAWINGS

For a better understanding of the present invention, reference may be had to the following detailed description taken in conjunction with the accompanying drawings in which:

FIGS. 3-6, illustrate a method of control of an air flow pump in accordance with the teaching of the present invention.

DETAILED DESCRIPTION OF THE INVENTION

Figure 1:
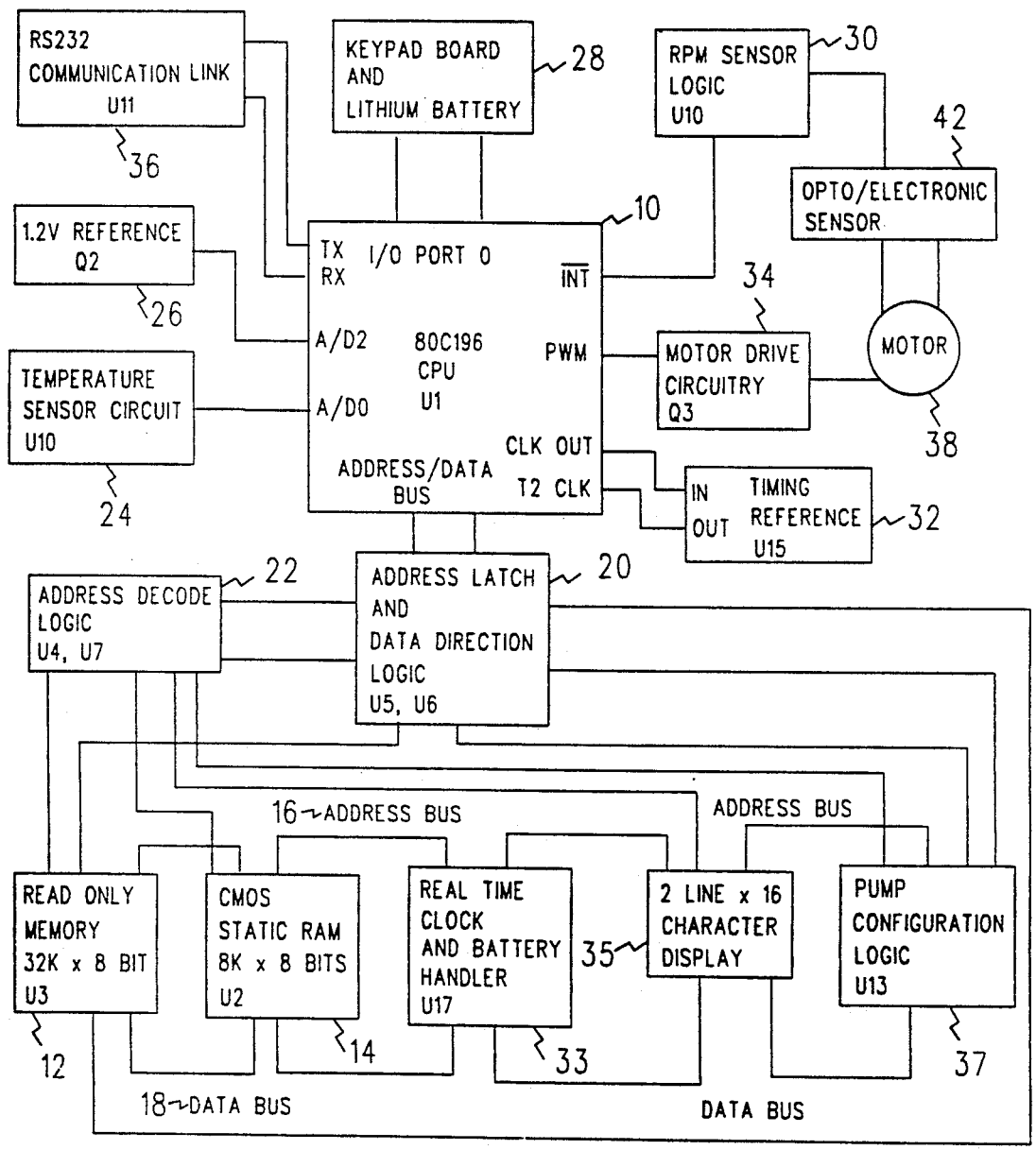
FIG. 1 is a simplified block diagram of a microcomputer controlled pump motor in accordance with the present invention.

FIG. 1 illustrates a block diagram of one implementation of the present invention. This implementation is based upon a microprocessor and, in particular, a type 80C196 central processor unit (CPU) indicated at 10 having read only memory (ROM) 12 and random access memory (RAM) 14 connected via address bus 16 and data bus 18 through an address latch and data direction logic circuit 20. An address decode logic circuit 22 is also connected onto the address bus and to various peripherals on the buses. The CPU 10 is connected via various I/O ports for receiving data input from a temperature sensor circuit 24, a voltage reference 26, a keyboard 28, an RPM sensor logic 30, and a timing reference 32. A real time clock 33 and a pump configuration logic circuit 37 are also connected to the CPU 10. A 2 line ×16 character LCD display 35 is coupled to the data and address buses 16, 18. The CPU 10 includes internal logic circuits for generating PWM signals at an I/O port for delivery to a motor drive circuit 34 and a transmit (TX) and receive (RX) port for connection to a communication link 36. A rechargeable lithium battery is physically mounted to the keyboard and provides power to maintain CPU RAM in the event of loss of primary power. Primary power is provided by a rechargeable nickel-cadmium battery pack (not shown).

The motor driver circuit 34 is coupled in driving relationship to a direct current (DC) electric motor 38. A shaft of motor 38 is coupled to drive a bellows-type air pump 40 (FIG. 2), and an opto-electronic sensor 42 is positioned for providing an actual count of the revolutions per minute (RPM) of the motor shaft. Sensor 42 provides the RPM count to RPM sensor logic 30 which conditions the count to a form acceptable by CPU 10. An LCD display 35 provides direct readout of selected data including input data such as commanded or desired flow rates, PWM and RPM values, and various status messages and error signals.

Figure 2:
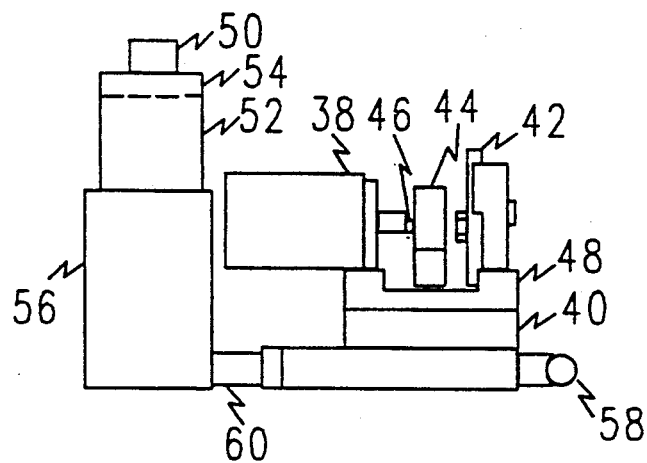
FIG. 2 is an elevation view of a pump, motor, RPM sensor, and input filter and damper arrangement for an air sampling pump.
Figure 2A:
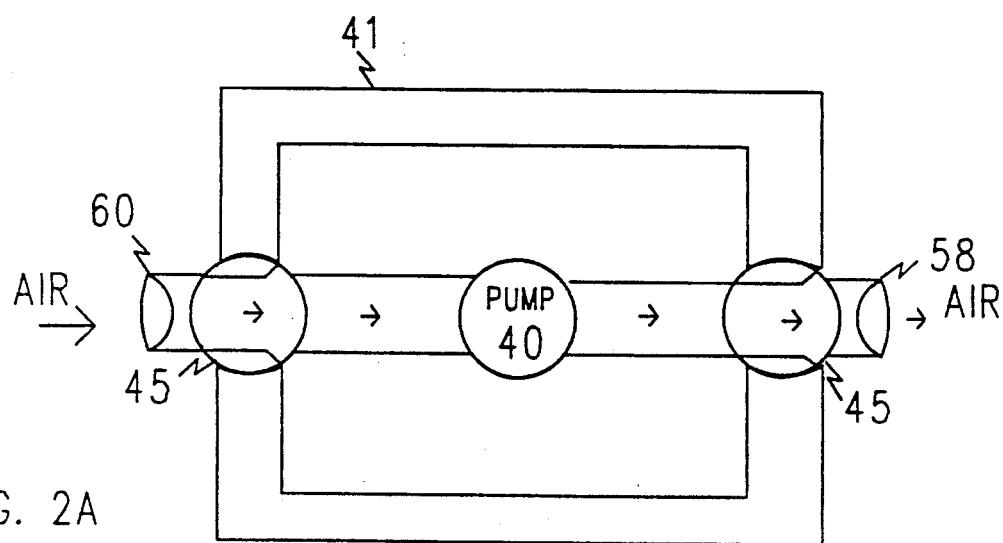
FIGS. 2A and 2B are simplified schematic representations of a pump bypass arrangement with arrows indicating air flow for non-bypass and, high-bypass valve positions.
Figure 2B:
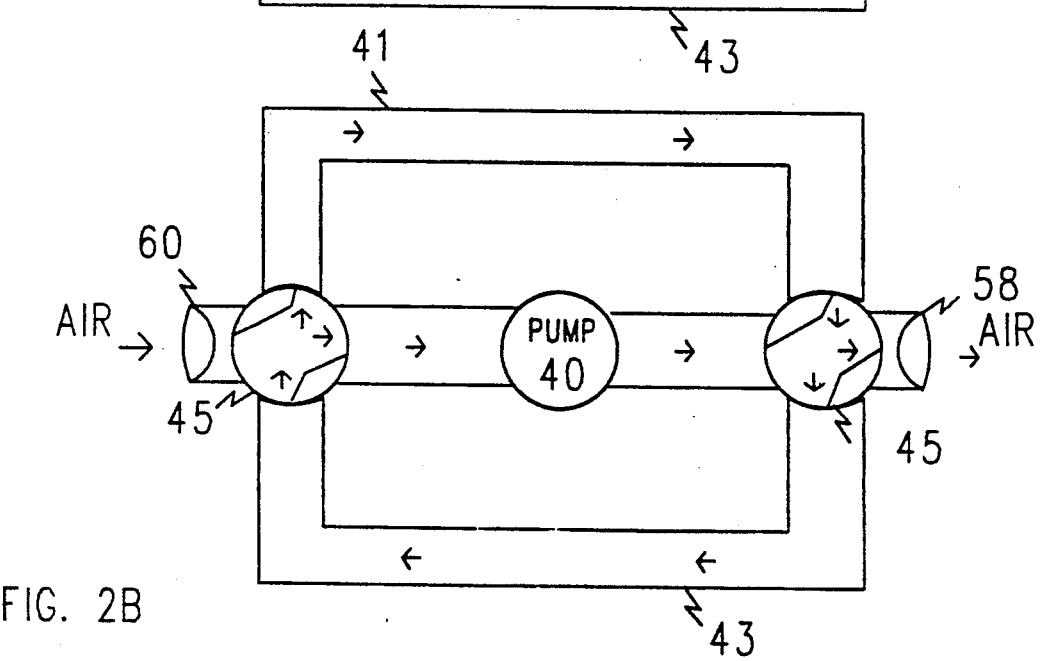
Figure 5:
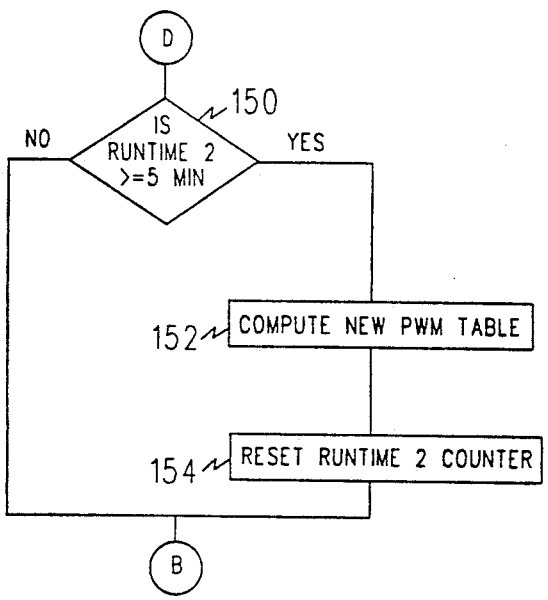
Figure 6:
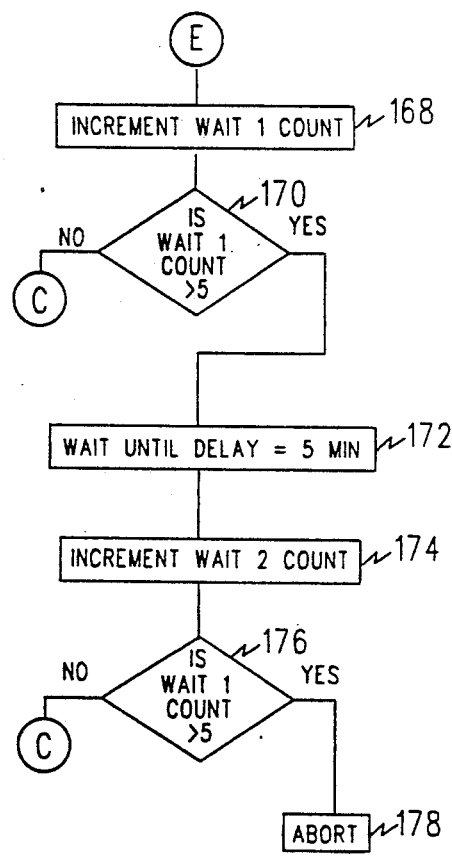

FIG. 2 is a simplified elevation view of the pump 40 illustrating the arrangement of motor 38 and sensor 42. The pump 40 may be a commercially available pump such as that available from CASSELLA Ltd. of England which uses a flexible diaphragm that can be driven by a cam actuated lever 44 coupled to motor shaft 46. The opto-electronic sensor 42 is mounted to pump body 48 adjacent lever 44 and opposite motor 38, also mounted to pump body 48. An air inlet 50 is formed as part of a support 52 for an inlet filter or particulate collector 54. Air passing through filter 54 enters a damper 56 which tends to smooth pulsations created by operation of the diaphragm type pump. The damper 56 may be a chamber formed with at least one wall of a thin flexible material such as Neoprene rubber. Exhaust air exits through exhaust port 58. The pump 40 includes bypass lines 41, 43 and bypass valve 45 (FIGS. 2A and 2B) which allows air to circulate around the pump from the exhaust port to inlet line 60. The bypass valve is adjusted to provide a high bypass for very low flow rates, i.e., 5 cc/minute, and is closed for rates within the range of control through the pump. The valve 45 may comprise a spindle or shaft having suitable ridges and notches for directing air flow to selected passages. FIG. 2A illustrates the spindle 45 rotated so that all air passes through the pump 40 and none through bypass lines 41, 43. FIG. 2B illustrates spindle valve 45 in an open position such that a preselected portion of the air circulates through lines 41, 43. FIG. 2B is used for low flow rates, i.e., rates between five and 500 cubic centimeters per minute. This high bypass/low flow rate mode is needed primarily for air or gas sampling using well known charcoal tube samplers (not shown). Such samplers include a sample holder adapted for fitting onto a tubular hose, such as is used to connect to inlet 50, and which is generally referred to in the industry as Tygon tubing. The charcoal tube sample holders are supplied with multi-turn adjusting needle valves for flow control. When in the low flow sampling mode, the valve spindle 45 is in the open position of FIG. 2B and the motor 38 is set to run at a constant RPM. Air flow is then adjusted using an air flow standard such as the Buck Calilogger flowmeter by adjustment of the needle valve on the sample holder. The pump speed is thereafter maintained constant so that air flow is held constant. The use of constant speed pump operation in low flow mode is believed to eliminate "pulsing" which has been characteristic of many prior art systems. Furthermore, use of such constant speed pumping may negate the need for the damper 56 and thus reduce the cost of such systems.

In a high flow mode, i.e., air flow rates greater than about 500 cc/minute, the sample filter is typically a membrane type filter designed to capture larger size particulate. The sample filter, whether membrane or charcoal, is attached to an end of a tube (not shown) extending from pump inlet 50. The sample holder with its filter is normally clipped to a person's shoulder area as near as possible to the air being inhaled without inhibiting the person's movements. The filter 54 is a protective filter for the pump 40 and serves to prevent damaging particles from entering the pump.

The present invention regulates air flow indirectly, i.e., by controlling RPM of the pump motor 38. In the high flow mode, i.e., for flow rates greater than about 500 cc/minute, motor speed is varied to establish a desired flow rate. Through empirical testing, a relationship is established between air flow, pulse width modulation (PWM), and motor RPM. This relationship can be plotted as two separate curves, one relating RPM to air flow and another relating RPM to PWM. For use in the microcomputer system of FIG. 1, these curves can be generated as tables and stored in memory. Since each pump and filter combination may require a different table of values, Applicants have found that a base curve, normalized for a preselected value, can be stored in ROM and utilized to generate a substantially exact relationship for a specific pump and filter combination by establishing two points on the curve. Preferably, the single table, which is stored in RAM, is generated using a high PWM value and a low PWM value. Using the 80C196 CPU, values between 0 and 255 can be used for PWM counts, i.e., in a one second interval, full voltage to the motor is represented by 255/256 and zero voltage is represented by 0/256. However, for establishing the curve, it is desirable to use a high PWM count of about 224 and a low PWM count of about 48. The high PWM value of 224 allows room on the high side for compensation when the pump or filter 54 begins to get clogged. The low PWM value is selected to be the lowest PWM value which does not normally stall out the pump motor (determined through trial and error). The motor is turned on to the high PWM flow rate, and the user is prompted to utilize a flow calibration meter, such as the Buck Calilogger meter, to measure the actual flow. The user then enters the flow rate into the CPU 10 (either by directly scrolling the number up/down on the display 35, or indirectly via the communication link 36 connected to an external read-out apparatus such as the Buck Calilogger meter). After entering the high PWM data, the motor 38 is energized at the low PWM setting, and the process is repeated. The CPU reads RPM values while the user is making the flow measurement readings. Thus, a direct correlation between PWM, flow rate, and RPM is attained for two points on a curve.

The base curve stored in ROM (or EPROM) 12 for both RPM and flow rate contains a relative percentage of value versus the high and low values. Specifically, for a value n found in the table, the actual value can be computed as:

Flow Rate = (High Rate − Low Rate) × (n/100) + Low Flow Rate

RPM Count = (High RPM − Low RPM) × (n/100) + Low RPM

The actual data based on the two calibration points is computed and loaded into RAM 14. Thus, after calibration, a table exists within RAM 14 containing the computed flow rate and RPM values for all possible PWM values. The user now specifies the desired flow rate for sampling, and the CPU 10 scans the table until it finds the value exactly, or finds the next table value bigger than the desired flow rate. The corresponding PWM value is then sent to the motor drive circuit 34, causing the motor 38 to run at approximately the desired RPM. The accuracy of the sampling flow rate depends directly on the accuracy of the calibration data entered by the user. The ROM 12 relative percentages have four digits of precision.

In an ideal world, the initial PWM value output would deliver a steady flow rate during the entire sampling period. However, as the filter 54 becomes full, it clogs, which decreases the air flow through the filter, loads the motor 38, and decreases its RPM. The relationship between RPM drop and flow drop is not linear, however, and varies with air flow rate. Thus, a special compensation loop is provided to keep air flow at a fairly constant rate. The compensation is performed in two loops, an inner loop which updates the PWM output value once every 15 seconds, and an outer loop which updates the target RPM value every five minutes.

The flow rate table, i.e., flow rate vs. RPM, is used only to determine the initial PWM value. After that, the RPM-to-PWM table is used exclusively. The inner loop has two portions, a three second kink detection portion and a fifteen second compensation loop. The kink detection logic looks for a drop or rise in the RPM count from the expected/nominal count found in the RAM table, i.e., the RPM value corresponding to the PWM value supplied to motor 38. If the delta RPM value exceeds either of two thresholds (approximately 15% down, 10% up), the pump motor is de-energized for three seconds and a warning message is displayed to the user on display 43. The pump motor is then re-energized for three seconds to see if the situation has improved and returned to normal. If not, the motor is again turned off and the warning message displayed. This six second on/off cycle continues for five cycles, after which the cycle becomes three seconds on, one minute off. This also repeats for five cycles. Finally, the cycle is extended to three seconds on, five minutes off, again repeating the cycle up to five times. If the situation has not corrected itself at this point, the motor is turned off and an "abort" error message is displayed. The advantage of this kink detection technique is the low battery drain during an extended retry period, in addition to reactivation of the pump after the kink/filter-removal problem has been corrected. Note that during kink processing, the normal compensation logic is not performed.

The inner fifteen second compensation loop actually provides most of the control for steady flow. It takes the RPM count reading for the past fifteen seconds and compares it against the nominal RPM count value from the RAM table. If the RPM count is too high, a lower PWM value is output to compensate for it. If the RPM count is too low, a higher PWM value is output to compensate for it. The new PWM value is integrated into the actual PWM value that is output, being weighted using predetermined gain factors.

The outer five minute compensation loop is present to handle the steady clogging of the filter 54. This is expected to be a very gradual process, which may have virtually no effect on air flow in many applications. However, when filter interference does reduce air flow, the output PWM value to the motor will be increased (by the inner loop) to keep the RPM's and hence the air flow up. The outer loop modifies the RAM flow rate table, correcting the values to take into account the decreased flow per PWM unit. The updated table is then used by the inner loop. This keeps the internal model of the flow characteristics consistent with the real world flow characteristics. It also tends to reduce the error commands from the inner loop. Note, this is an approximation to constant flow, not constant RPM, because the RPM to flow values change as the filter clogs (is updated as such in the RAM table). This is not constant flow, however, because flow rate is not directly measured, but inferred from knowledge of how RPM relates to flow.

Turning now to FIGS. 3-6, there is shown a simplified flow chart setting forth the method of operation of the system of FIG. 1 as discussed above. The flow chart assumes that the user has energized the system and connected a flow cell such as the Buck Calilogger to the system in order to provide initial flow test data. The system is initially placed in a programming mode (block 100) through keyboard entries utilizing keyboard 28 or via the serial link 36 through an external flow metering device such as the Buck Calilogger. Once in programming mode, the maximum flow test (block 102) is first selected and the pump motor energized at the first selected high value such as a PWM rate of 224. After the maximum flow test has been completed resulting in storage of data corresponding to the RPM and flow rate at the selected PWM value, the minimum flow test (block 104) is then selected and the system energized at a minimum PWM rate such as, for example, 40 counts. Upon completion of the minimum flow test, the system automatically constructs the flow rate vs. RPM table and the RPM vs. PWM table (block 106). At this time, the user enters the desired flow rate (block 108) from the keyboard 28 or from the serial link 36 via an external flow metering device such as the Buck Calilogger, and the program energizes the pump motor to what it believes is the desired flow rate. The external flow metering device such as the Buck Calilogger may be used to determine actual flow rate (block 110), which will be displayed on the 2 line ×16 character LCD display 35. After the pump is de-energized at the conclusion of the desired flow test, the duty cycle information is input (block 112). The duty cycle is specified for one hour period in twelve intervals corresponding to the twelve five minute periods within that hour. Each five minute period may be individually specified to have the pump on or off during that period. After the duty cycle data has been input, the pump operation start time is input (block 114). If the input start time is 00:00, the program will start pump operation using the programmed duty cycle immediately after entering sampling mode (block 122). If the input start time is not 00:00, the program will wait after entering sampling mode (block 124) until the system's internal battery-backed twenty-four hour clock shows the time equal to the programmed start time. After start time has been input, if input is arriving via the keyboard 28, the external flow metering device may be removed and sampling mode must be selected using the keyboard 28 (block 118). If input is arriving via the serial link 36 from an external flow metering device such as the Buck Calilogger, additional duty cycle information is input, regarding the start time and duration of three break periods and a total desired pump operation time (block 120). After these extra duty cycle values have been received, the external flow metering device may be removed and the program automatically enters sampling mode.

In sampling mode, the system selects the corresponding RPM value for the desired flow rate (block 126), and from that the corresponding PWM value (block 128). The pump motor is then energized using the selected PWM value (block 130), and after two seconds (block 132), the actual RPM value is accessed (block 134) and compared to the selected RPM value (block 136), as determined at block 126. The program first determines whether the difference in RPM is greater than preselected limits. The limits may be a speed increase of greater than 10% or a speed decrease of greater than 15% (block 136). If the speed increases by a value larger than the upper range limit, it can be assumed that the pump 40 and associated motor 38 have become unloaded. This may occur if, for example, an external particulate filter has become detached from the inlet hose to the air inlet 50. A decrease in motor RPM may indicate a clogged filter or kinked hose. If the RPM is not outside of the preselected upper and lower limits, a plurality of cycle or wait counters is then reset (block 138). A plurality of run time counters is then updated (block 140) to show another three seconds have elapsed. The program then determines if the run time 1 counter has exceeded fifteen seconds (block 142). If so, the system compensates the PWM value so as to adjust the RPM value to the original selected value (block 144). The run time 1 counter is reset (block 146), and the PWM error accumulated in a RAM register (block 148). As was discussed above, the accumulated PWM error is used to modify the RPM vs. PWM table to compensate for a slowly clogging filter 54. The program next checks to determine if the pump run 2 counter is greater than five minutes (block 150). If the run time 2 counter is less than five minutes, the program loops back to the selected PWM (block 128) and again begins its cycle. If the run time 2 counter is greater than or equal to five minutes, the program computes a new RPM vs. PWM table based upon the accumulated PWM error over the past five minutes (block 152). The new RPM table is then used to replace the original computed RPM vs. PWM table. Once the new table has been established, the program resets the run time 2 counter (block 154) and again loops back to select a PWM value (block 128).

If at block 136 it was determined that the actual RPM of the motor 38 exceeded the established limits, the run time 1 counter is reset (block 156) and the pump motor is de-energized (block 158). The program then waits for three seconds (block 160), and increments a counter (block 162). The system now determines if the counter has been incremented more than five times (block 164). If not, the system loops back to block 130 and again energizes the motor 38. The blocks 156, 158, 160, and 162 constitute the three second on, three second off cycle discussed previously.

If it is determined in block 164 that the wait or cycle counter has exceeded five counts, the system goes into a second stage of cycling in which the motor is energized for three seconds and de-energized for one minute intervals. When the motor is de-energized at block 158, the program steps through blocks 156, 158, 160, and 162 to arrive at block 166 where it waits with the motor de-energized for one minute. Another counter is incremented to count the number of times that the program steps through the one minute wait cycles (block 168). If the block 168 counter is not greater than five counts (block 170), the program will return to block 130 to again energize the motor. If the RPM of the motor continues to be outside the limits for more than five times through block 170, block 170 will detect that the counter is greater than five and run the program into a five minutes off cycle (block 172). A third counter is then incremented with the number of times that the program goes through the five minute cycle (block 174), and a block 176 indicates tracking of the number of times through the five minute cycle. At the end of each five minutes, the system will attempt to energize the motor at the selected RPM and again determine whether or not the actual RPM is within the preselected range of the selected RPM, i.e., loops back to block 130. If the cycle continues through more than five counts of the five minute wait periods, the system will then abort (block 178).

It will be appreciated that what has been described is a control system for an air sampling pump and a method of operating the pump and system. In particular, there has been described a method for controlling an air sampling pump in a system in which a CPU 10 develops PWM control signals for application to a PWM motor driver 34. The motor driver 34 is connected to an electric motor 38 which is coupled in driving relationship to a bellows-type air pump 40. An RPM counter is coupled to the motor for providing RPM signals representative of air flow through the pump. Electronic memories 12 and 14 are coupled to the CPU 10 for storing data indicative of relationship between RPM, PWM, and air flow such that the CPU 10 can respond to a commanded air flow by generating a corresponding PWM signal which will cause the motor to drive the pump at an RPM selected to produce the commanded air flow. In the method of operation, the pump is energized at a preselected PWM value and the flow rate and RPM corresponding to that PWM value are determined. The pump is then energized at another preselected PWM value different than the first value and the flow rate and RPM corresponding to the second PWM value are recorded. The CPU 10 then computes a table of values from the information obtained from these first two tests by extrapolating from the measured values to preselected normalized values stored in ROM memory. In this manner, the CPU 10 is able to establish a direct relationship between motor RPM and air flow rate. The user then sets a desired flow rate for the pump system using the keyboard entry system for the CPU and reading the data being set in on the display 35. The CPU, in turn, generates a first PWM signal for energizing the pump and motor 38 at an RPM corresponding to the desired flow rate using the values in the table of PWM vs. RPM settings. The CPU monitors the RPM of the pump and periodically adjusts the PWM value in such a manner as to maintain the RPM at a value corresponding to the desired flow rate. The CPU 10 continues to compare the actual difference between the first PWM value and a last periodically adjusted PWM value to a preselected difference value and if that actual difference exceeds the preselected difference, it recomputes the table of values relating RPM to PWM by adjusting the RPM values proportionately to the actual difference between the first and last PWM values. As described above, the recomputing of the table of values relating RPM to PWM occurs at periodic intervals such as, for example, five minutes.

The CPU also monitors changes in the actual RPM of the motor which exceeds a preselected magnitude and de-energizes the pump motor when the magnitude is exceeded. In one cycle, the system will maintain the pump motor in its de-energized condition for a first preselected time interval such as three seconds and thereafter re-energizes the pump motor for a second preselected time interval such as, for example, three seconds. If the actual RPM change continues to exceed the preselected magnitude, the CPU will switch to a different cycle and begin de-energizing the pump motor for longer periods. In one form, the CPU will de-energize the pump motor for a preselected time interval of one minute and then re-energize for three seconds. If repetitive de-energizations of one minute and re-energizations of three seconds occur for more than a preselected count, such as, for example, five counts, than the system will step to a third mode of correction in which the motor will be de-energized for a longer preselected period, such as, for example, five minutes. If the CPU 10 fails to determine that the RPM is within the selected range after this last time interval has been repeated for a preselected count, the system will then abort and provide an error message indicating the amount of time that the pump actually operated.

The process of cycling the pump off for longer and longer periods is selected to minimize battery drain in the event that the hose to the pump inlet has been kinked. This allows the pump to be restarted by an operator if the kinking is corrected and without having to be concerned that the battery may have run down due to the excess load during the time that the hose may have been kinked.

Each 50 msec, after the keypad has been scanned and processed, a battery validation routine is called which reads the battery A/D value and converts it into a percentage of maximum value. The A/D input utilizes the 80C196 built-in A/D conversion facilities. The A/D is told to input the battery voltage. After delaying at least eight clock cycles, the program enters a tight loop which is exited when the A/D input is complete, as shown by bits in the A/D Status Register. The ten bit A/D value is accessed and saved in RAM. A conversion table is located in EPROM, which lists the battery voltage for 100% charge, 95% charge, 90% charge, etc., all the way down through 0% charge. The table is scanned from the top, comparing the input battery voltage value to the table values, stopping when the battery voltage value is greater than a table value (or the end of the table is reached). The corresponding battery capacity percentage is based simply on which entry was last tested, i.e., if the battery voltage is lower than the third entry (90%) but equal to or higher than the fourth entry (85%), the battery capacity will be 85%. This gives a battery resolution of 5%.

If the battery capacity percentage is below 5%, a message is output to the display for five seconds, after which the unit automatically turns itself off to prevent damage to the batteries themselves. If the capacity is 15% or lower, but higher than 10%, a warning message is displayed to the user, which requires an explicit knowledge (via a push of the ENTER/ACCEPT key) from the user before the active state is reentered. A complication to this approach is the correct re-output of the display to its pre-warning contents. This has been handled by returning a flag from the routine, showing whether the warning message was displayed. Each calling routine must test this flag, and if set, take individualized steps to regenerate the display.

It will be appreciated that the system described above simplifies the air sampling system by eliminating the need for flow measurement devices in the air sampling pump. Instead, the air flow is empirically determined from the RPM of the motor driving the air pump. While the invention has been described in what is presently considered to be a preferred embodiment, various modifications and arrangements will become apparent to those skilled in the art. It is intended, therefore, that the invention not be limited to the illustrative embodiment but be interpreted within the full spirit and scope of the appended claims.

What is claimed is:

1. A method for controlling an air sampling pump in a system including a central processing unit (CPU) for developing pulse width modulated (PWM) control signals for application to a PWM motor driver connected to an electric motor, the motor being coupled in driving relationship to the air pump, a revolution per minute (RPM) counter coupled to the motor for providing RPM signals representative of air flow to the CPU, and a memory operatively associated with the CPU for storing data indicative of relationships between RPM, PWM, and air flow, the CPU being responsive to a commanded air flow for generating a corresponding PWM signal, the method comprising the steps of:
    (a) energizing the pump at a preselected PWM value and determining the pump flow rate and RPM corresponding to the PWM value;
    (b) energizing the pump at another preselected PWM value different than the first named PWM value and determining the pump flow rate and RPM corresponding to the another PWM value;
    (c) computing, in the CPU, tables of PWM values relating RPM and flow rate to PWM values for a range of values including the first named and the another PWM values from the determined RPM and flow rate at the first named and the another PWM value;
    (d) setting a desired flow rate for the pump and generating a first PWM signal for energizing the pump at an RPM corresponding to the desired flow rate from values in the tables of PWM values; and (e) monitoring the RPM of the pump and periodically adjusting the first named PWM value to an adjusted value to maintain the RPM at a value corresponding to the desired flow rate.

2. The method of claim 1 further including the steps of:

(f) comparing the actual difference between the first PWM value and the last periodically adjusted PWM value to a preselected difference value; and, if the actual difference exceeds the preselected difference, (g) recomputing the table of values relating RPM to PWM by adjusting the RPM values proportionately to the actual difference between the first and last PWM values;

(h) selecting a new first PWM signal; and (i) periodically repeating step (f) of comparing through step (h) of selecting.

3. The method of claim 1 and further including the steps of:

(j) detecting a change in the actual RPM exceeding a preselected magnitude and de-energizing the pump motor in response thereto;

(k) maintaining the pump motor in its de-energized condition for a first preselected time interval and thereafter re-energizing the pump motor for a second preselected time interval;

(l) determining if the actual RPM change continues to exceed the preselected magnitude and, if so, again de-energizing the pump motor; and (m) repeating step (k) of maintaining and step (l) of determining for a first preselected number of cycles.

4. The method of claim 3 and subsequent to the repeating step thereof the further steps of:

(n) maintaining the pump motor in its de-energized condition for a third preselected time interval longer than said first time interval and thereafter re-energizing the pump motor for a fourth preselected time interval;

(o) determining if the actual RPM change continues to exceed the preselected magnitude and, if so, de-energizing the pump motor for the third preselected time interval; and (p) repeating step (n) of maintaining and step (o) of determining for a second preselected number of cycles.

5. The method of claim 4 and subsequent to the step (p) of repeating, the additional steps of:

(q) maintaining the pump motor in its de-energized condition for a fifth preselected time interval longer than said third time interval and thereafter re-energizing the pump motor for a sixth preselected time interval;

(r) determining if the actual RPM change continues to exceed the preselected magnitude and, if so, de-energizing the pump motor for the fifth preselected time interval; and (s) repeating step (q) of maintaining and step (r) of determining for a third preselected number of cycles.

* * * * *